United States Patent [19]

Johansen

[11] Patent Number: 5,434,345
[45] Date of Patent: Jul. 18, 1995

[54] POTATO VARIETY ND671-4RUSS

[75] Inventor: Robert H. Johansen, Fargo, N. Dak.

[73] Assignee: North Dakota State University, Fargo, N. Dak.

[21] Appl. No.: 615,165

[22] Filed: Nov. 19, 1990

[51] Int. Cl.$^6$ .......................... A01H 5/00; A01H 5/04
[52] U.S. Cl. .......................................... 800/200; 47/58; 47/DIG. 1; 800/DIG. 42; 800/DIG. 71
[58] Field of Search ............. 47/58, DIG. 1; 800/200, 800/DIG. 42, 71

[56] References Cited

U.S. PATENT DOCUMENTS 4,696,674  9/1987  Cipar .................................... 800/200
4,723,052  2/1988  Cochran ............................... 800/200
4,795,705  1/1989  Gressel et al. ....................... 800/200

Primary Examiner—James R. Feyrer
Attorney, Agent, or Firm—M. Reid Russell

[57] ABSTRACT

The new potato variety Solanum tuberosum ND671-4RUSS is a cross of Wash.330 and ND9567-2RUSS. It was first grown at the horticulture greenhouse on the campus of North Dakota State University. The new variety produces tubers that are oblong, smooth, and uniform with shallow eyes and dark brown skin that are suitable for use as french fries and for fresh use. The variety has some resistance to scab and has fairly good resistance to *Verticillium wilt*.

3 Claims, 4 Drawing Sheets

POTATO VARIETY ND671-4RUSS

BACKGROUND OF THE INVENTION

1. Field of the Invention

The present invention relates to a new and distinct variety of potato Solanum tuberosum which was discovered by me growing at the Langdon Research Center located at Langdon, N. Dak.

2. Prior Art

The new potato variety was produced from a cross made by me in the horticulture greenhouse on the campus of North Dakota, with a seedling tuber also produced in the same horticulture greenhouse and at Glyndon, Minn. The new variety, ND671-4RUSS resulted from a cross between a Wash. 330 and a ND9567-2RUSS.

University colleagues, breeders and seedsmen who have seen this potato do not recognize this selection as anything that they have previously selected or evaluated. The potato variety has been classified as a cross of a Wash. 330 and ND9567-2RUSS. Selection and initial evaluation was done as set out above, with evaluations being done at the Langdon Research Center, Langdon, N. Dak., and horticulture greenhouse on the campus of the North Dakota State University. Preliminary testing in variety trails began in 1982 and commercial trials were initiated and held in Park River, Grand Forks, and Williston, N. Dak. from 1985 to 1989.

BRIEF SUMMARY OF THE INVENTION

The plants of the new variety of potato hereinafter referred to as ND671-4RUSS are fairly large in size and are upright. The stems are dark green in color and have purple streaks generally near the base of the plants. The leaves are medium in size and are dark green in color. The flowers are white. The base of the corolla is large and white in color with green buds. The plant flowers profusely with good viable pollen.

The tubers of ND671-4RUSS are long in type and are fairly heavily russeted. Shape however, can vary depending on the soil they are produced in. The tuber are smooth and have shallow eyes. Yields of ND671-4RUSS grown at two locations in North Dakota showed this variety to be better or comparable to the standard russet skinned varieties, Norgold Russet, NorKing Russet and Russet Norkotah and much better than Russet Burbank.

The dry matter or total solids of ND671-4RUSS is comparable to Russet Burbank but higher than Norgold Russet and Russet Norkotah. High total solids is desirable for both processing and fresh table use.

The selection ND671-4RUSS has some resistance to Verticillium wilt and to common scab. It is susceptible to late blight *phytophtora infestans*. When grown in most areas, ND671-4RUSS is excellent for processing into frozen french fries. Test have indicated that it is better or comparable to the standard variety Russet Burbank.

DETAILED DESCRIPTION OF THE INVENTION

Figure 1:
FIG. 1 shows a true as is reasonably possible, a plant and leaf types of ND671-4RUSS grown at North Dakota State University.

The following is a detailed description of the new variety of potato Solanum tuberosum, hereinafter referred to as ND671-4RUSS. Color terminology as set out herein is to be accorded its ordinary dictionary significance except where otherwise indicated. The described tubers and plants were grown at Glyndon, Minn. and in the greenhouse at North Dakota State University:

Plant, as shown best in FIG. 1,: Large and upright.

Stems: Green pigmented, purplish particularly near the base of the plant.

Wings: Medium but prominent in size, reach the entire way or distance to the next node and are generally straight.

Nodes: Prominent.

Internodes: Green with purple streaks.

Stipules: Small non-clasping.

Leaves: Medium in size compared to Russet Burbank and Russet Norkotah, but small compared to NorKing Russet and Norchip. Dark green, moderately pubescent.

Terminal Leaflets: Elliptical; oblique apex cuspidate; asymmetrical; length 83.3 mm±0.1, width 47.9 mm±0.05.

Primary Leaflets: Elliptical; apex cuspidate; asymmetrical; 2 to 3 pairs. Length 75.2 mm±1.0, width 47.7 mm±0.6.

Secondary Leaflets: Common.

Tertiary Leaflets: Common.

Midriffs and Petioles: Light green; sparsely pigmented; slightly pubescent.

Flowers: White and abundant.

Buds: Green.

Calyx: Long, straight, very pubescent.

Corolla: Large, white.

Anthers: Orange with abundant pollen and of good quality.

Style: Straight.

Stigma: Roughly round, single lobed, and green.

Figure 2:
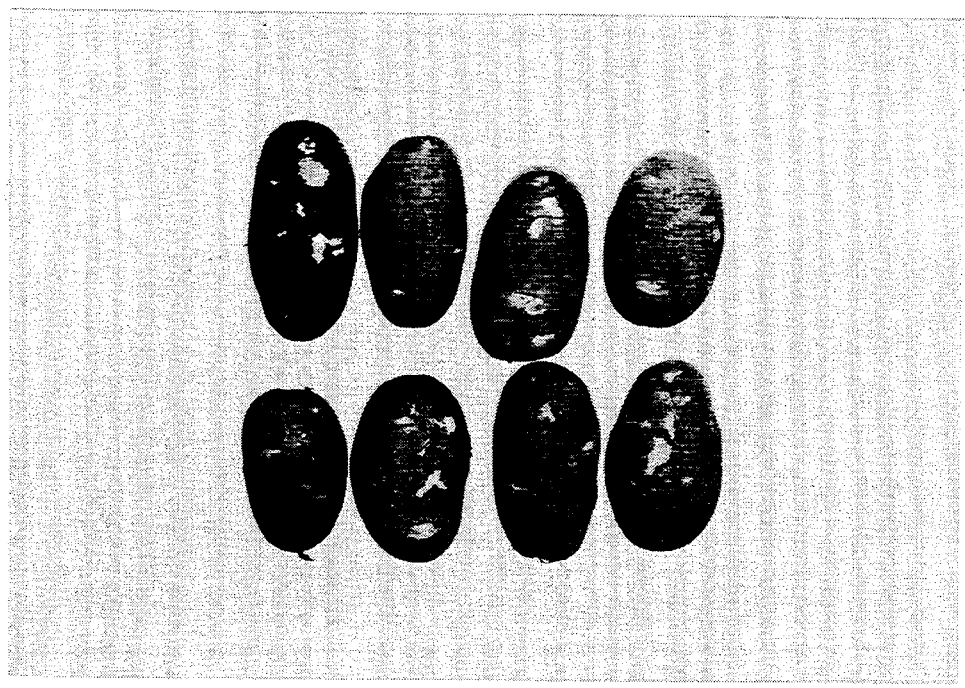
FIG. 2 shows as true as is reasonably possible, typical tubers of ND671-4RUSS grown at 1989 commercial trials at Grand Forks, N. Dak.
Figure 3:
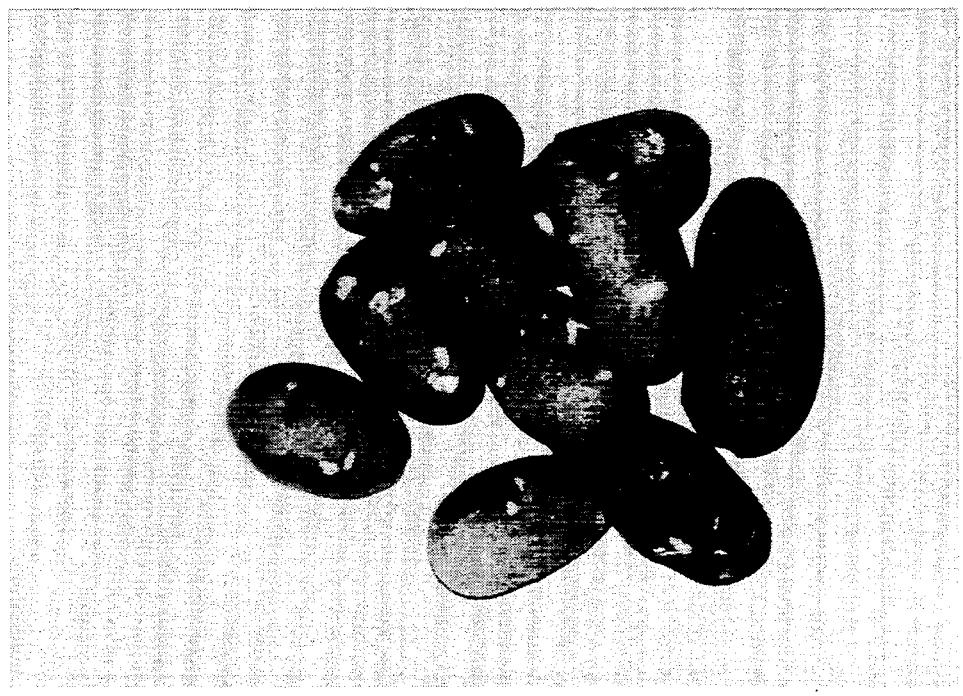
FIG. 3 shows as true as is reasonably possible, typical tubers of ND671-4RUSS, like those of FIG. 2 grown at 1989 commercial trials at Grand Forks, N. Dak.

Tubers, as shown best in FIGS. 2 and 3: Are oblong; thirty (30) tuber samples were measured and found to have a mean length of 104.0 mm., a mean width of 62.8 mm., with a mean thickness of 58.1 mm.

Indices for the above thirty (30) tuber samples: Width to length 0.60; thickness to length 0.56; thickness to width 1.18; average number of tubers per plant 8.

Skin: Dark brown; heavy russeted.

Eyes: Shallow and well distributed.

Flesh: White.

Sprouts: White with purple tip.

Maturity: Medium; later than Russet Norkotah but much earlier than Russet Burbank.

Characteristics: Tubers are usually smooth and uniform. However ND671-4RUSS is susceptible to hollow heart if weather and growing conditions are such as to be conducive to hollow heart. Very few external or internal defects have been observed.

Uses: ND671-4RUSS is comparable to or better than Russet Burbank for use as french fries. Tests conducted by the Food and Nutrition Department, Home Economics Department of the University of North Dakota have also shown that ND671-4RUSS is excellent for fresh use, such as by boiling and/or baking.

Yields: Five (5) year tests in North Dakota (see Tables below) have shown ND671-4RUSS to be higher in yield than Norking Russet, Russet Norkotah, and Russet Burbank, but not as high as Norgold Russet. In the North Central Regional Potato Trials, ND671-4RUSS was higher in yield than the 15 check varieties.

Disease Resistance: ND671-4RUSS is susceptible to most potato virus diseases and early to late blight. HD671-4RUSS has, however, some resistance to scab and has fairly good resistance to *Verticillium wilt*.

A germ plasm of ND671-4RUSS, *solanum tuberosum* is deposited with the American Type Culture Collection (ATCC), Rockville, Md., accorded an Accession Number (ATCC) 75884, which deposit is made under the conditions of the Budapest Treaty and provide that:
(a) during the pendency of this application access to the invention will be afforded to the Commissioner upon request;
(b) all restrictions upon available to the public will be irrevocable removed upon granting of a patent on this application;
(c) the deposit will be maintained in a public depository for a period of thirty (30) years, or five (5) years after the last request, or for the effective life of a patent issued on this application, whichever is longer; and
(d) the deposit will be replaced should it become inviable.

Figure 4:
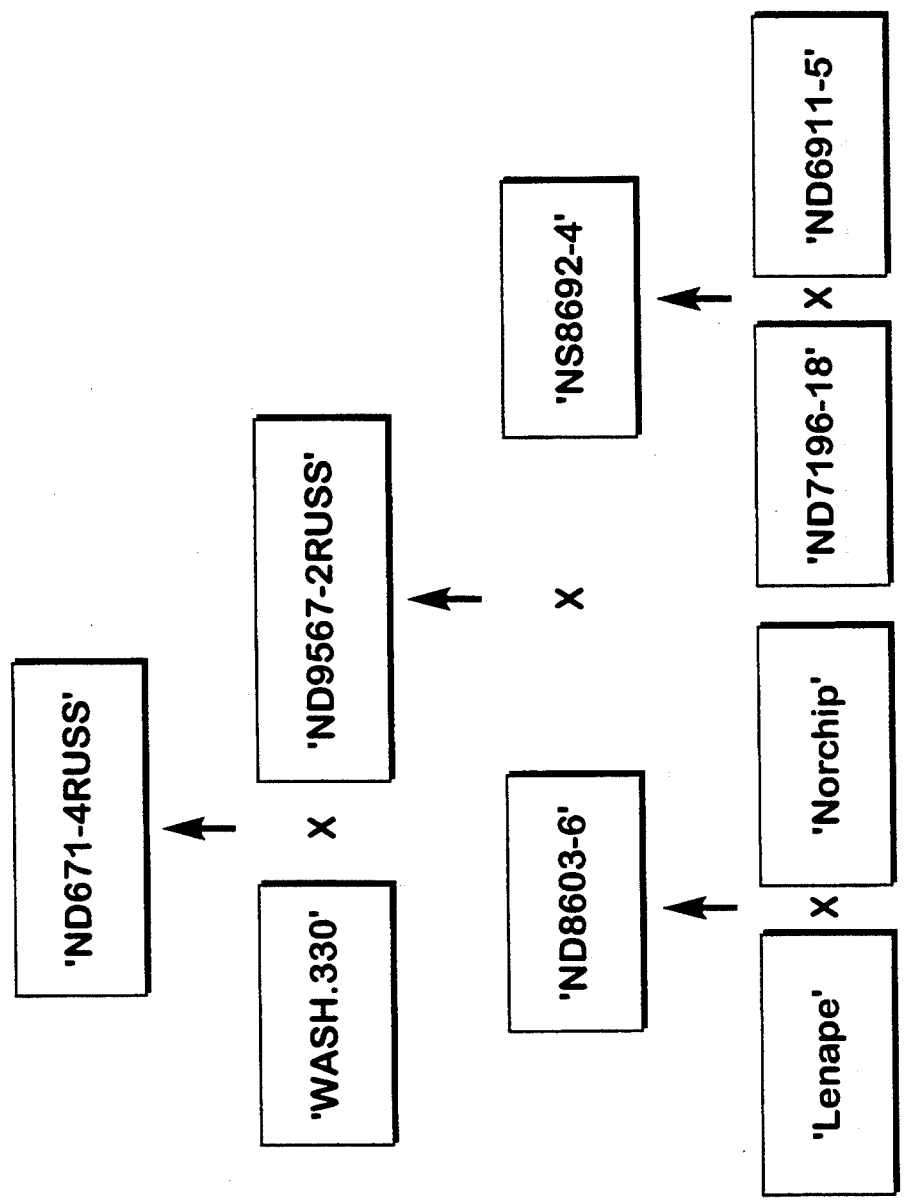
FIG. 4 shows as true as is reasonably possible, a pedigree chart of ND671-4RUSS.
Figure 5:
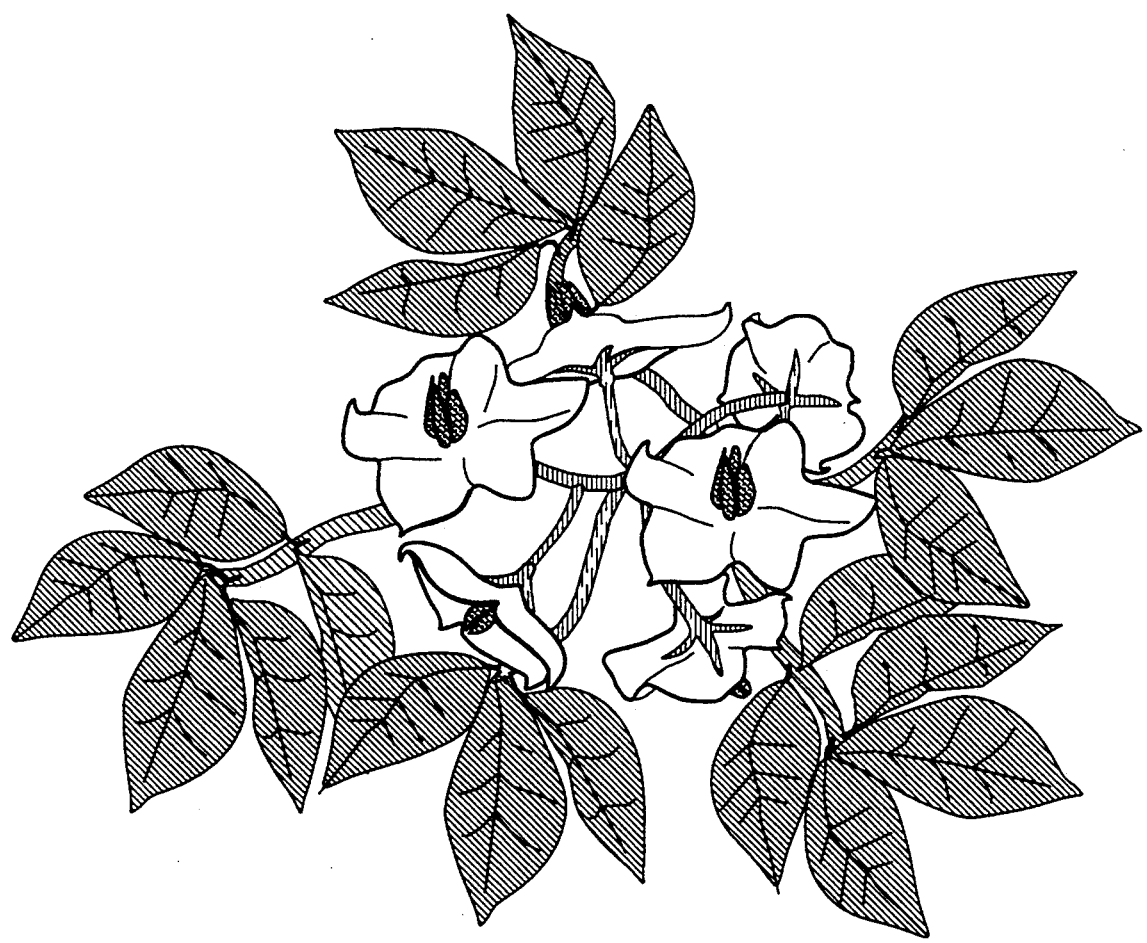
FIG. 5 shows a drawing of the ND671-4RUSS, with components thereof shown cross hatched utilizing drawing symbols set out in 37 CFR 1.84 for identifying the colors of which plant components.

A pedigree of ND671-4RUSS as shown in FIG. 4

IDENTIFICATION OF THE POTATO VARIETIES IN THE PARENTAGE OF ND671-4RUSS

1. Wash.330—A Washington selection, no longer available.
2. ND9567-2RUSS—AND advance selection, no longer available.
3. ND8603-6—AND advance selection, no longer available.
4. ND8692-4—AND advance selection, no longer available.
5. ND7196-18—AND selection, no longer available.
6. ND6911-5—AND selection, no longer available.
7. Norchip—Formerly ND 5899-1, Nomed in 1968, a NDSY variety.
8. Lenape—Formerly B5141-6 has been, withdrawn as a variety.

TABLES

Herein are included Table 1 and 2 that detail ND671-4RUSS characteristics for yield and total solids for the years 1985-1989 grown and tested at Grand Forks and Park River, N. Dak.

TABLE 1

U.S. NO. 1 YIELD (CWT/A) OF ND671-4 RUSS AND FOUR CHECK POTATO VARIETIES GROWN AT TWO LOCATIONS - PARK RIVER (PR) AND GRAND FORKS (GF), ND.

|  | 1985 | | 1986 | | 1987 | | 1988 | | 1989 | | AVERAGE | |
| --- | --- | --- | --- | --- | --- | --- | --- | --- | --- | --- | --- | --- |
|  | GF cwt/a | PR cwt/a | GF cwt/a | PR cwt/a | GF cwt/a | PR cwt/a | GF cwt/a | PR cwt/a | GF cwt/a | PR cwt/a | GF cwt/a | PR cwt/a |
| ND671-4 Russ | 204 | 243 | 176 | 233 | 224 | 222 | 98 | 129 | 205 | 138 | 181 | 193 |
| Norgold Russet | 181 | 216 | 192 | 214 | 240 | 273 | 81 | 178 | 173 | 194 | 173 | 215 |
| NorKing Russet | 191 | 187 | 141 | 242 | 225 | 192 | 143 | 155 | 114 | 177 | 163 | 191 |
| Russet Norkotah | 161 | 193 | 220 | 301 | 261 | 232 | 85 | 178 | 197 | 155 | 156 | 212 |
| Russet Burbank | 144 | 161 | 187 | 156 | 92 | 156 | 24 | 33 | 53 | 88 | 100 | 119 |

TABLE 2

PERCENT TOTAL SOLIDS OF ND671-4 RUSS AND FOUR CHECK POTATO VARIETIES GROWN AT TWO LOCATIONS -- PARK RIVER (PR) AND GRAND FORKS (GF), ND

|  | 1985 | | 1986 | | 1987 | | 1988 | | 1989 | | AVERAGE | |
| --- | --- | --- | --- | --- | --- | --- | --- | --- | --- | --- | --- | --- |
|  | GF % | PR % | GF % | PR % | GF % | PR % | GF % | PR % | GF % | PR % | GF % | PR % |
| ND671-4R | 20.7 | 21.2 | 19.9 | 18.4 | 19.2 | 19.9 | 19.0 | 21.2 | 19.2 | 19.0 | 19.6 | 19.9 |
| Norgold Russet | 19.9 | 21.4 | 18.6 | 20.1 | 19.4 | 20.1 | 16.9 | 20.9 | 18.6 | 18.8 | 18.7 | 20.3 |
| NorKing Russet | 21.8 | 22.2 | 21.6 | 19.4 | 19.9 | 20.9 | 20.9 | 22.0 | 18.8 | 19.9 | 20.6 | 20.9 |
| Russet Norkotah | 20.1 | 20.3 | 19.0 | 20.7 | 19.4 | 19.7 | 17.5 | 20.9 | 19.2 | 18.6 | 19.0 | 20.0 |
| Russet Burbank | 22.2 | 21.8 | 21.4 | 20.9 | 19.4 | 18.8 | 18.6 | 19.0 | 18.2 | 17.3 | 20.0 | 19.6 |

Hereinabove has been set out a new variety of potato, *Solanum tuberosum*, identified as ND671-4RUSS including its physical characteristics and qualities. It should, however, be understood that the present disclosure is made by way of example only and that variations are possible within the scope of this disclosure without departing from the subject matter coming within the scope of the following claims, and a reasonable equivalency thereof, which claims I regard as my invention.

I claim:

1. A new and distinct variety of potato plant identified as ND671-4RUSS and deposited with ATCC under Accession No. 75884, resulting from the cross of Wash. 330 and ND9576-2RUSS, being particularly characterized in comparison to the commercial russet potato varieties Norgold Russet, Russet Burbank, Russet Norkotah, and NorkKing Russet by the combination of traits comprising:

an upright habit of large size with medium open habit; having dark green, moderately pubescent leaves and stems of green pigmentation which have purple streaks;

producing abundant flowers having large corollas of white coloration and having anthers with abundant orange, fertile pollen, straight styles, roughly round, single lobed and green stigmas;

producing an average of 6 to 8 tubers per plant which, under normal conditions, are oblong, smooth, and of uniform shape, with uniform, shallow eyes, dark brown skin, a heavy russet, white flesh, of high quality for use in french fries, mashing and baking; and the plant having some resistance to scab and having good resistance to *Verticillium wilt*.

2. The new and distinct variety of potato plant of claim 1 in the growth stage of tubers.

3. The new and distinct variety of potato plant of claim 1 in the form of propagating material.

* * * * *